United States Patent
Redaelli et al.

(10) Patent No.: US 10,961,492 B2
(45) Date of Patent: Mar. 30, 2021

(54) MICROFLUIDIC DEVICES AND RELATED METHODS FOR GENERATION AND/OR CULTURE AND/OR MATURATION OF THREE-DIMENSIONAL CELLS AND/OR TISSUE CONSTRUCTS

(71) Applicants: POLITECNICO DI MILANO, Milan (IT); FONDAZIONE CARIPLO, Milan (IT)

(72) Inventors: Alberto Redaelli, Milan (IT); Marco Rasponi, Milan (IT); Paola Occhetta, Romentino (IT)

(73) Assignees: POLITECNICO DI MILANO, Milan (IT); FONDAZIONE CARIPLO, Milan (IT)

( * ) Notice: Subject to any disclaimer, the term of this patent is extended or adjusted under 35 U.S.C. 154(b) by 271 days.

(21) Appl. No.: 15/567,204

(22) PCT Filed: Apr. 28, 2016

(86) PCT No.: PCT/IB2016/052410
§ 371 (c)(1),
(2) Date: Oct. 17, 2017

(87) PCT Pub. No.: WO2016/174607
PCT Pub. Date: Nov. 3, 2016

(65) Prior Publication Data
US 2018/0105782 A1    Apr. 19, 2018

(30) Foreign Application Priority Data

Apr. 29, 2015   (IT) ................. 10201513538

(51) Int. Cl.
*C12M 3/06*     (2006.01)
*C12M 3/00*     (2006.01)
*C12M 1/00*     (2006.01)
*C12M 1/12*     (2006.01)
*C12M 1/42*     (2006.01)

(52) U.S. Cl.
CPC ............ *C12M 23/16* (2013.01); *C12M 21/08* (2013.01); *C12M 23/32* (2013.01); *C12M 23/34* (2013.01);
(Continued)

(58) Field of Classification Search
CPC ...... C12M 23/16; C12M 23/34; C12M 23/32; C12M 35/04; C12M 35/02; C12M 25/02; C12M 21/08
See application file for complete search history.

(56) References Cited

U.S. PATENT DOCUMENTS

2008/0194012 A1* 8/2008 Lee .................. B01L 3/502707
                                                          435/287.1
2009/0088342 A1    4/2009 Moraes et al.
(Continued)

FOREIGN PATENT DOCUMENTS

EP    2071189 A1    6/2009
EP    2184344 A1    5/2010
(Continued)

OTHER PUBLICATIONS

Agarwal, A. et al., "Microfluidic heart on a chip for higher throughput pharmacological studies", Lab Chip, 13(18), Sep. 21, 2013, pp. 3599-3608 (DOI: 10.1039/c3lc50350j).
(Continued)

*Primary Examiner* — Michael L Hobbs
(74) *Attorney, Agent, or Firm* — MH2 Technology Law Group, LLP

(57) ABSTRACT

A microfluidic device for controlled generation and/or culture and/or maturation of three-dimensional cells and/or tissue constructs that includes a culture chamber may include: a confinement apparatus configured to define at least one compartment configured to contain a cellular matrix and at least one compartment configured to contain a
(Continued)

culture medium, the confinement apparatus being hydrophobic and pervious to the culture medium; and/or at least one counter element. The confinement apparatus and at least one counter element may be reciprocally mobile between resting and compression positions of the cellular matrix. A method for controlled generation and/or culture and/or maturation of three-dimensional cells and/or tissue constructs at a microscale may include: controlled compression of a cellular matrix for a predetermined period of time. The cellular matrix may be delimited by a confinement apparatus that is pervious to a culture medium.

20 Claims, 6 Drawing Sheets

(52) U.S. Cl.
CPC ............ *C12M 25/02* (2013.01); *C12M 35/02* (2013.01); *C12M 35/04* (2013.01)

(56) References Cited

U.S. PATENT DOCUMENTS

| 2012/0231533 | A1* | 9/2012 | Holl | ................. | C12M 23/12 |
| | | | | | 435/287.9 |
| 2013/0295601 | A1* | 11/2013 | Park | ................. | G01N 33/5026 |
| | | | | | 435/32 |

FOREIGN PATENT DOCUMENTS

| EP | 2647434 A1 * | 10/2013 | .......... B01F 11/0048 |
| EP | 2647434 A1 | 10/2013 | |
| WO | 2010/148275 A2 | 12/2010 | |
| WO | 2012/139715 A1 | 10/2012 | |

OTHER PUBLICATIONS

International Search Report and Written Opinion dated Jul. 28, 2016, in corresponding International Application No. PCT/IB2016/052410, 12 pages.

Duffy, D. et al., "Rapid Prototyping of Microfluidic Systems in Poly(dimethylsiloxane)", Analytical Chemistry, American Chemical Society, vol. 70, Jan. 31, 1998, pp. 4974-4984.

Agarwal, A. et al., "Microfluidic heart on a chip for higher throughput pharmacological studies", Lab Chip, 13(18), Sep. 21, 2013, pp. 3599-3608.

Huang, C.P. et al, "Engineering microscale cellular niches for three-dimensional mutlicellular co-cultures", Lab Chip, 9 (12), Jun. 21, 2009, pp. 1740-1748.

Mathur, A. et al., "Human iPSC-based Cardiac Microphysiological System for Drug Screening Applications", Scientific Reports, 5, Mar. 9, 2015, pp. 1-7.

* cited by examiner a b c

MICROFLUIDIC DEVICES AND RELATED METHODS FOR GENERATION AND/OR CULTURE AND/OR MATURATION OF THREE-DIMENSIONAL CELLS AND/OR TISSUE CONSTRUCTS

CROSS-REFERENCE TO RELATED APPLICATION(S)

This application is a national stage entry from International Application No. PCT/IB2016/052410, filed on Apr. 28, 2016, in the Receiving Office ("RO/IB") of the International Bureau of the World Intellectual Property Organization ("WIPO"), published as International Publication No. WO 2016/174607 A1 on Nov. 3, 2016, and claims priority under 35 U.S.C. § 119 from Italian Patent Application No. 102015000013538, filed on Apr. 29, 2015, in the Italian Patent and Trademark Office ("IPTO"), the entire contents of all of which are incorporated herein by reference.

TECHNICAL FIELD

The present invention relates to the field of biomedical sciences and pharmacology, more specifically microfluidics, and refers to a new microfluidic device for the controlled generation and/or culture and/or maturation of microscale three-dimensional cell and/or tissue constructs and a new method for the controlled generation and/or culture and/or maturation of microscale three-dimensional cell and/or tissue constructs.

TECHNICAL BACKGROUND

It is known that in the pharmaceutical field, the development and subsequent marketing of a drug implies a complex, slow and extremely costly process which comprises various testing phases of the drug.

In particular, a pre-clinical testing phase and four clinical testing phases can be distinguished: a clinical pharmacological phase: phase I; an effectiveness study phase: phase II; a multicentre study phase: phase III; and finally phase IV for studies carried out after the marketing of the drug. The pre-clinical phase and clinical phases represent 63% and 32% respectively of the costs of the development of a drug.

In the pre-clinical phase, the active ingredient of the drug is tested on an experimental model of the disease which comprises in vitro models (for example cell cultures) and in vivo models (i.e. on animals). In the subsequent clinical testing phases from I to IV, the tests are carried out on human beings.

Both of the above models of the pre-clinical phase, however, are subject to criticism: the in vitro models on cell cultures, often of an animal origin, do not always allow to predict the behaviour of the drug in vivo, i.e. in a situation in which the tissue is in interaction with the whole living system.

One of the reasons for this limited prediction capacity can be attributed to the fact that the traditional in vitro models mainly consist of cell monolayers cultivated on flat rigid substrates. It is recognized in the field, however, that more reliable responses can be obtained with the use of engineered models, i.e. which are capable of exhibiting characterizing features of the native tissues, such as, for example, the three-dimensional nature of the cell adhesion environment and the reproduction of mechanical properties more similar to the natural ones.

Furthermore, it is known that also due to inter-species differences, in terms of, for example, ionic channels, metabolic pathways and pharmacokinetic properties, in vitro animal models are not sufficiently reliable in the study of a drug intended for human beings.

Depending on the type of testing to be performed, the availability of the necessary cells, especially if human, can also represent an obstacle, in particular in the case of tissues having a limited regenerative capacity, such as, for example, cardiac and nervous tissues. This gives rise to a problem of the availability of cells, especially human cells, and consequently of the reliability of the testing owing to the limits of the resources available.

In vitro testing therefore suffers from the drawback of often representing a first screening which is too approximate, far from inexpensive, and that does not always prove to be sufficiently predictive of the behaviour of the same active ingredient in vivo in human beings.

In vivo testing on animals, on the other hand, also draws criticism, in particular based on the incompatibility of the animal model with respect to the human physiology, the intrinsic variability of the model itself and the considerable expenses associated with the management of the many animals involved, including their maintenance and care, in addition to the costs of the samples themselves of the drug or active ingredient to be tested, which are not negligible.

In addition, there are also ethical considerations relating to the treatment and fate of the animals themselves, which impose a series of restrictions for safeguarding their well-being. Furthermore, in the last few decades, a progressive public awareness has emerged, on both a national and international scale with respect to the above ethical issue, to which the scientific community itself is increasingly conforming to, when possible, in finding valid alternatives to the massive in vivo testing on animals. Analogously, in the field of medical sciences and biomedical and tissue engineering, in particular in the field of research, it is known to use tissue constructs originating from animal and human cells as three-dimensional models for the study and treatment of human diseases.

The models currently available, however, suffer from the same limitations discussed above with respect to in vitro models.

Huang et al. (2009) describe a microfluidic device for the cultivation of three-dimensional cultures capable of mimicking the in vivo microenvironment. The device comprises a microfluidic channel made of a polymeric matrix containing the cell culture whose perimeter is defined by two rows of pillars interposed between two culture medium reservoirs. The internal structure of the device occupies the whole internal height of the same device. This device, however, does not envisage any expedient for the mechanical stimulation of the cells. It is known, in fact, that the mechanical stimulation supplied to cell constructs is capable of enhancing the mechanical properties of the constructs themselves.

Agarwal et al. (2013) describe a "heart on a chip" device for the pharmacological study of cardiac tissue. It is based on the seeding of cardiomyocytes on thin cantilevers made of a soft material. This device, however, does not allow the generation of cardiac constructs that are representative of the native tissue, but instead the culture of cells in monolayers, as it is based on two-dimensional cultures.

Mathur et al. (2015) describe a microscale cardiac microphysiological system that uses the three-dimensional confinement for seeding high-density pluripotent cardiac cells inside a microfluidic channel, facilitating its arrangement in a three-dimensional beating construct. This device, however, does not allow the formation of an actual tissue construct as the cells are not distributed on a scaffold but cultivated in a culture medium in a housing, without any supporting matrix. Furthermore, this system does not envisage any mechanical stimulation methods.

The necessity is therefore felt in the above fields for providing an effective and reliable cell tissue model for in vitro testing, which overcomes the drawbacks of the known art.

More specifically, there is the need to provide a method and a device for drug screening and development at a pre-clinical level which is effective and economical and which at the same time allow to overcome the drawbacks of the known art.

The technical problem at the basis of the present invention is therefore to provide a device and a method that allow cell and/or tissue constructs to be obtained, that overcome the drawbacks of the known art.

In particular, an object of the present invention is to provide such a device (and such a method) that is effective, reliable, simple and economical to use, and simple and economical to produce.

A further technical problem at the basis of the present invention is to provide such a device and such a method that allow mature tissue constructs to be obtained, and that overcome the drawbacks of the known art.

SUMMARY OF THE INVENTION

The above technical problem has been solved, according to the present invention, by a microfluidic device suitable for the controlled generation and/or culture and/or maturation of a three-dimensional cell and/or tissue construct comprising a culture chamber comprising:
a) confinement means defining at least one compartment suitable for containing a cellular matrix and at least one compartment suitable for containing a culture medium, said confinement means being hydrophobic and pervious to the culture medium; and
b) at least one counter element;
wherein the confinement means and the at least one counter element are reciprocally mobile between a resting position and a compression position of the cellular matrix.

The expression "microfluidic device" refers herein to a system equipped with at least one channel for the microscale confinement and movement of fluids (volumes of fluids comprised between units of femtoliters and hundreds of microliters).

The expression "cellular matrix" refers herein to a cell culture, a three-dimensional tissue construct, and/or any intermediate stage thereof, such as for example a three-dimensional cell construct.

The expression "three-dimensional cell construct" refers herein to a mass of cells structurally bound to each other, either directly or by means of a polymeric structure. Such a structure can be of a natural origin, of synthetic origin, or a combination thereof.

The expression "three-dimensional tissue construct" refers herein to a mass of cells functionally bound to each other, capable of no longer responding only individually but also as a functional syncytium.

The expression "cell culture" refers herein to a cell suspension or aggregate in a medium kept viable and grown outside of their native environment.

The expression "controlled generation and/or culture and/or maturation" refers herein to the stages of the transformation process of an initial cell culture into a three-dimensional cell and/or tissue construct by means of a device and a process wherein the stimuli suitable for favouring it are adjustable and repeatable.

Preferably, said three-dimensional tissue construct is mature.

The term "mature" means herein that the three-dimensional tissue construct substantially consists of cells in an advanced differentiation stage and has a behaviour similar to the native behaviour of the tissue of which a construct is to be obtained.

Preferably, the cell matrix comprises a natural or synthetic polymer, or a combination thereof, more preferably a fluid polymeric solution and/or a gel, even more preferably a hydrogel.

Preferably, the fluid polymer solution comprises polymers selected from the group comprising fibrin, collagen, hyaluronic acid, elastin, fibroin, agarose, chitosan, alginate, and the like, and mixtures thereof, more preferably fibrin.

Preferably, the hydrogel is selected from the group comprising fibrin gel, collagen, collagen gelatin, hyaluronic acid, elastin, fibroin, agarose, chitosan, alginate, and the like, and combinations thereof, more preferably fibrin gel.

Preferably, the cellular matrix has a behaviour which includes an elastic component.

The term "resting position" or "resting step" means herein that the cellular matrix is not subjected to compression or is subjected to a lower compression with respect to that to which the same is subjected in the compression position.

For the comparison of the compression degree of the cellular matrix in the compression position (or step) with respect to the resting position (or step) and/or before the compression step, the percentage of reduction in the thickness of the cellular matrix in the compression position (or step) with respect to the same dimension in the resting position (or step) and/or before the compression step, is used. The percentage of the extension of a dimension of the cellular matrix in the compression position (or step) with respect to the same dimension in the resting position (or step) and/or before the compression step, is also used.

The term "counter element" refers herein to a structural element of the culture chamber of the device which, as it is in contact with the cellular matrix in the compression position, causes its compression.

Preferably, in the compression position, the at least one counter element is in abutment with the confinement means.

Preferably, the confinement means are realized on a supporting wall of the confinement means of the culture chamber.

Preferably, the confinement means are positioned on at least part of the perimeter of the compartment suitable for containing a cellular matrix.

The perimeter of the compartment suitable for containing a cellular matrix preferably has a regular geometrical shape, more preferably a regular polygon, even more preferably a rectangle, even more preferably a microfluidic channel.

The term "microfluidic channel" refers herein to a duct suitable for confining a fluid and having at least one dimension comprised between 1 μm and 1000 μm. Unless otherwise specified, it is understood that the shape of the perimeter of the microfluidic channel is substantially rectangular.

Preferably, the length or width of the microfluidic channel corresponds to the length or width of the culture chamber.

Preferably, the microfluidic channel has a width comprised between 20 and 2,000 μm, more preferably comprised between 100 and 500 μm, even more preferably 300 μm; and a length comprised between 50 μm and 20 mm, more preferably comprised between 200 μm and 10 mm, even more preferably about 3 mm.

With the term "hydrophobic", relating to the confinement means, it is understood herein that these are made of a material in itself hydrophobic or rendered such by means of chemical and/or physical surface treatment.

Preferably, the confinement means are made with a chemically inert material, more preferably selected from silicon rubber, for example polydimethylsiloxane (PDMS), fluorinated rubber, polystyrene (PS), polymethyl methacrylate (PMMA), polycarbonate (PC), glass, silicon, polyethyleneglycol (PEG), and the like, and combinations thereof, more preferably silicon rubber.

Preferably, the confinement means have a height less than the thickness of the cellular matrix.

Preferably, the confinement means comprise a plurality of micropillars.

Preferably, the micropillars are positioned in rows, more preferably at a distance between adjacent micropillars comprised between 5 μm and 250 μm, more preferably comprised between 15 μm and 100 μm, even more preferably about 50 μm.

Preferably, the adjacent micropillars are equidistant with respect to each other.

Preferably, the micropillars are pillars of any shape in section, preferably having a polygonal or circular section with height dimensions comprised between 20 and 400 μm, more preferably comprised between 80 and 200 μm, even more preferably about 100 μm, and a radius or a side of the polygon comprised between 5 and 100 μm, more preferably comprised between 20 and 60 μm, even more preferably about 30 μm.

Preferably, the micropillars have the same size as each other.

Preferably, the length of a row of micropillars is comprised between 50 μm and 20 mm, more preferably comprised between 200 μm and 10 mm, most preferably about 3 mm.

Preferably, the micropillars are positioned in two parallel rows so as to define a microfluidic channel.

Preferably, the distance between two parallel rows of micropillars, or the width of the microfluidic channel that they define, is comprised between 100 and 2000 μm, more preferably comprised between 200 and 400 μm, even more preferably about 300 μm.

Preferably, the micropillars are positioned in two or more parallel rows so as to define a plurality of microfluidic channels, more preferably parallel to each other.

Preferably, a microfluidic channel is divided into a plurality of microfluidic channels in series.

Preferably, in the compression position, the confinement means and the at least one counter element are in a closer position with respect to the resting position.

Preferably, the compression position is obtained by moving the at least one counter element and/or the supporting wall of the confinement means.

Preferably, the at least one counter element comprises a mobile wall, more preferably flexible.

Preferably, the moving is realized by means of an actuation of the type selected from pneumatic, hydraulic, mechanical, electrical, magnetic, thermal, and combinations thereof, more preferably a pneumatic actuation.

Preferably, the at least one counter element is made with a chemically inert material, more preferably elastically deformable, most preferably selected from silicon rubber, for example polydimethylsiloxane (PDMS), fluorinated rubber, polystyrene (PS), polymethyl methacrylate (PMMA), polycarbonate (PC), glass, silicon, polyethyleneglycol (PEG), and combinations thereof, more preferably silicon rubber.

In a preferred embodiment, in the resting position, the supporting wall of the confinement means and the plane formed by the at least one counter element are substantially parallel.

In an alternative embodiment, in the compression position, the supporting wall of the confinement means and the plane formed by the at least one counter element are substantially parallel.

Preferably, in the resting position, the minimum distance between the confinement means and the plane formed by the at least one counter element is comprised between 1 μm and 250 μm, more preferably comprised between 10 μm and 70 μm, most preferably 50 μm.

Preferably, in the resting position, the minimum distance between the confinement means and the plane formed by the at least one counter element is comprised between 1 and 90%, more preferably between 15 and 50%, even more preferably of about 35% with respect to the overall height of the culture chamber.

Preferably, the microfluidic chamber is produced longitudinally to the supporting wall of the confinement means of the culture chamber, along the centre of its width.

Preferably, the culture chamber has height dimensions comprised between 20 μm and 500 μm, more preferably comprised between 100 μm and 250 μm, most preferably 150 μm; a width comprised between 150 μm and 5000 μm, more preferably comprised between 500 μm and 2500 μm, most preferably 1600 μm; and a length comprised between 50 μm and 20 mm, more preferably between 200 μm and 10 mm, most preferably about 3 mm.

Preferably, each part of the device is made with a chemically inert material, more preferably selected from silicon rubber, for example polydimethylsiloxane (PDMS), fluorinated rubber, polystyrene (PS), polymethyl methacrylate (PMMA), polycarbonate (PC), glass, silicon, polyethyleneglycol (PEG), and combinations thereof, preferably silicon rubber.

Preferably, the device is suitable for compressing the cellular matrix cyclically, more preferably at a frequency comprised between 0.05 and 50 Hz, more preferably comprised between 0.5 and 5, most preferably about 1 Hz.

Advantageously, in the compression position, the device is suitable for imparting to the cellular matrix a reduction in its thickness comprised between 1 and 90% with respect to the thickness of the same in resting position, more preferably comprised between 15 and 50%, even more preferably about 35%.

Preferably, in the compression position, the device is suitable for imparting to the cellular matrix an extension of at least one dimension thereof comprised between 1 and 100% with respect to the same dimension of the cellular matrix in resting position, more preferably comprised between 5 and 20%, even more preferably about 10%.

Preferably, the extension of the cellular matrix is a uniaxial extension.

The expression "uniaxial extension" means herein that the extension substantially takes place in only one dimension of the cellular matrix.

Preferably, the confinement means are suitable for confining the cellular matrix in a microfluidic channel and creating a uniaxial extension of the cellular matrix in the direction of the width of the microfluidic channel.

Advantageously, the compression is controlled, i.e. the compression, as well as the reduction in thickness and the extension of the cellular matrix deriving therefrom, is adjustable and repeatable.

According to a preferred embodiment, the device comprises an actuation chamber suitable for causing a movement of the at least one counter element towards the cellular matrix suitable for compressing the cellular matrix, preferably by means of pneumatic or hydraulic actuation.

Preferably, the movement of the at least one counter element towards the cellular matrix consists in a flexion or a deflection of the counter element.

Preferably, the actuation chamber is separated from the culture chamber by the wall comprising the at least one counter element.

Preferably, the actuation chamber comprises supporting means of the at least one counter element suitable for sustaining the at least one counter element in a resting position.

Preferably, the supporting means comprise at least one row of micropillars positioned between the at least one counter element and the wall opposite with respect to the direction of the movement of the at least one counter element towards the cellular matrix.

Preferably, the actuation chamber comprises a fluid in its interior, preferably a liquid, and even more preferably a saline solution.

Preferably, the actuation chamber is suitable for causing the movement of the at least one counter element towards the cellular matrix by means of a pressure increase inside the actuation chamber.

In a preferred embodiment, the pressure inside the actuation chamber in a resting position is atmospheric pressure and, in a compression position, is comprised between 0.01 atm and 10 atm, more preferably comprised between 0.1 and 1 atm, most preferably about 0.5 atm.

In an alternative embodiment, the pressure inside the actuation chamber in a resting position is negative, comprised between −1 atm and −0.01 atm and, in a compression position, comprised between 0 atm and 10 atm, more preferably comprised between 0.1 and 1 atm, most preferably about 0.5 atm.

Preferably, the actuation chamber is suitable for causing the movement of the at least one counter element cyclically.

Advantageously, the microfluidic device comprises one or more openings for the injection of the cellular matrix, and also for the entry and exit of the culture medium.

Preferably, the microfluidic device comprises at least one inlet for the application of the pressure and/or for introducing the fluid into the actuation chamber.

Preferably, the microfluidic device comprises housings for electrodes.

Preferably, the device is obtained by means of microfabrication techniques, more preferably lithographic techniques, even more preferably photo- and soft-lithographic techniques.

In a preferred embodiment, the device is assembled following the production of a plurality of parts obtained with microfabrication techniques.

In a particular embodiment, such parts obtained with microfabrication techniques are three parts and correspond to those illustrated in FIG. 3a.

In a particular alternative embodiment, such parts obtained with microfabrication techniques are two parts which, once joined, form the culture chamber and walls and supporting means of the actuation chamber. In this embodiment, the parts thus assembled can then be attached to a plane, even produced by different techniques. See FIG. 4, in which the parts a) and b) are produced with microfabrication techniques, and part c) is a plane.

In an alternative embodiment, the device is obtained in a single piece.

The present invention also relates to a method for the controlled generation and/or culture and/or maturation of a three-dimensional cell and/or tissue construct at the microscale comprising at least one step of controlled compression of a cellular matrix for a predetermined period of time, the cellular matrix being delimited by confinement means that are pervious with respect to a culture medium.

Preferably, the compression step is carried out cyclically, more preferably for a time comprised between 0.01 and 10 seconds, even more preferably between 0.1 and 1 second.

Consecutive compression steps are preferably interspersed with resting steps, more preferably having a duration comprised between 0.01 and 10 seconds, even more preferably comprised between 0.1 and 1 second.

Preferably, the compression step is repeated at a constant frequency of 0.05-50 Hz, more preferably 0.5-5 Hz, even more preferably 1 Hz.

Advantageously, the step of controlled compression of the cellular matrix causes a reduction in the thickness of the cellular matrix comprised between 1 and 90% with respect to the thickness of the same in the resting step and/or before the compression step, more preferably comprised between 15 and 50%, even more preferably about 35%.

Preferably, the step of controlled compression causes an extension of the cellular matrix in at least one dimension thereof comprised between 1 and 100% with respect to the same dimension of said cellular matrix in the resting step and/or before the compression step, more preferably comprised between 5 and 20%, even more preferably about 10%.

Preferably, the extension of the cellular matrix is a uniaxial extension.

Preferably, the step of subjecting the cellular matrix to compression is repeated at least until a three-dimensional cell construct, more preferably a three-dimensional tissue construct, is obtained, even more preferably until a mature three-dimensional tissue construct is obtained.

Preferably, the controlled compression step is realized by the reciprocal approachment movement of the confinement means and the at least one counter element from a resting position to a compression position of the cellular matrix, more preferably in abutment with respect to each other.

Preferably, the compression step (or position) is achieved by the movement of the at least one counter element towards the confinement means.

Preferably, the thickness of the cellular matrix is greater with respect to the height of the confinement means.

Preferably, the confinement means are made with a chemically inert material, more preferably selected from silicon rubber, for example polydimethylsiloxane (PDMS), fluorinated rubber, polystyrene (PS), polymethyl methacrylate (PMMA), polycarbonate (PC), glass, silicon, polyethyleneglycol (PEG), and the like, and combinations thereof, preferably silicon rubber.

Preferably, the cellular matrix has a behaviour which includes an elastic component.

Preferably, the cellular matrix comprises specialized cells or non-specialized cells, or combinations thereof.

Preferably, the cellular matrix comprises prokaryotic or eukaryotic cells, more preferably eukaryotic cells, even more preferably mammalian cells, most preferably human cells.

Preferably, the cells are stem cells or somatic cells, or a combination thereof.

Preferably, the stem cells are selected from the group that comprises embryonic and adult stem cells, more preferably pluripotent cells and induced pluripotent cells, even more preferably obtained from placenta, umbilical cord, adipose tissue, nervous tissue, muscle tissue, cardiac tissue, parenchymal tissues, epidermal tissue, and bone marrow tissue, and combinations thereof.

Preferably, the somatic cells are selected from the group that comprises cells derived from mesoderm, endoderm and ectoderm, more preferably endothelial cells, bone cells, cartilage cells, nerve cells, adipose cells, epithelial cells, fibroblasts, myofibroblasts, interstitial cells, hepatocytes, pancreatic cells, blood cells, muscle cells, and combinations thereof, more preferably muscle cells, even more preferably cardiac myocytes, primary cardiac myocytes, and/or combinations thereof, even more preferably primary cardiac myocytes from rats or obtained from human induced pluripotent cells.

Preferably, the cellular matrix comprises a natural or synthetic polymer, or a combination thereof, more preferably a fluid polymeric solution and/or a gel, even more preferably a hydrogel.

Preferably, the fluid polymeric solution comprises polymers selected from the group comprising fibrin, collagen, hyaluronic acid, elastin, fibroin, agarose, chitosan, alginate, and the like, and mixtures thereof, more preferably fibrin.

Preferably, the hydrogel is selected from the group comprising fibrin gel, collagen, collagen gelatin, hyaluronic acid, elastin, fibroin, agarose, chitosan, alginate, and the like, and combinations thereof, more preferably fibrin gel.

Preferably, the cellular matrix has a behaviour which includes an elastic component.

Preferably, the cellular matrix is confined in a plurality of microfluidic channels, more preferably parallel to each other, even more preferably positioned so that the cellular matrices comprised between them are not in reciprocal contact.

Preferably, the matrix is confined in a plurality of microfluidic channels, more preferably in series with respect to each other.

Preferably, the matrix is confined in a plurality of microfluidic channels, more preferably superimposed with respect to each other.

Preferably, the channels superimposed with respect to each other comprise cellular matrices that comprise different types of cells and/or polymers.

Preferably, the method of the present invention is carried out at a physiological temperature, more preferably at about 37° C. at atmospheric pressure for a time of up to 90 days, more preferably up to 21 days, most preferably seven days, under relative humidity conditions of 90% or higher, more preferably of 95% or higher, in an environment comprising 0-10% of $CO_2$, more preferably 5%, and comprising 0-25% of $O_2$, more preferably 20%.

Preferably, the three-dimensional cell and/or tissue construct is selected from the group comprising a cartilage construct, a muscle construct, a bone construct, a nerve construct, a connective construct, a fibrotic construct and combinations thereof, more preferably a muscle construct, even more preferably a cardiac construct.

Preferably, the tissue construct obtained is a mature three-dimensional tissue construct.

Preferably, the three-dimensional tissue construct is a beating cardiac construct. More preferably, the construct is a synchronously beating cardiac construct.

Preferably, the step of controlled compression comprises a step of regulation and/or evaluation of the maturation of the three-dimensional cell and/or tissue construct, preferably mature three-dimensional tissue construct, more preferably cardiac, by means of electrical stimulation, more preferably by means of electrodes associated to the construct, preferably imparting a pacing to the three-dimensional cell and/or tissue construct, more preferably the mature three-dimensional tissue construct, even more preferably the cardiac construct.

The term "pacing" refers herein to the regulation of the beat of the tissue construct by means of an external electric signal supplied by at least a pair of electrodes.

Preferably, the generation and/or culture and/or maturation are preferably carried out in the microfluidic device of the invention, and the method comprises the steps of:

a) making available the microfluidic device of the present invention;
b) seeding a cellular matrix in the compartment suitable for containing a cellular matrix;
c) introducing a culture medium into the at least one compartment suitable for containing a culture medium; and
d) incubating the microfluidic device thus arranged with the application of at least one step of controlled compression of the cellular matrix.

Preferably, in step b), the cellular matrix comprises a natural or synthetic polymer, or a combination thereof, more preferably a fluid polymeric solution.

Preferably, the fluid polymeric solution comprises polymers selected from the group comprising fibrin, collagen, hyaluronic acid, elastin, fibroin, agarose, chitosan, alginate, and the like, and mixtures thereof, more preferably fibrin.

Preferably, in step b), the cellular matrix is a cell culture.

Preferably, in step b), the cellular matrix comprises from $1\times10^2$ cells/µl to $1\times10^6$ cells/µl, more preferably about $1\times10^5$ cells/µl.

Preferably, in step b) of seeding a cellular matrix, a volume of cellular matrix comprised between 0.01 µl and 20 µl, more preferably about 0.5 µl, is introduced into the compartment suitable for containing the cellular matrix.

Preferably, step b) of seeding a cellular matrix is followed by a polymerization step of the cellular matrix, more preferably at 33-40° C. for 30 seconds-3 hours, even more preferably 5 minutes.

Preferably, following said polymerization step, the cellular matrix has a behaviour which includes an elastic component.

Preferably, the culture medium consists of a saline buffer solution (for example, at pH 7.4) containing essential amino acids, glucose and vitamins, more preferably Dulbecco/Vogt modified Eagle's minimal essential medium (DMEM).

Preferably, the culture medium contains serum antibiotics of an animal origin, and/or growth and cell differentiation factors.

Preferably, in step d) of incubating the device, the compression step of the cellular matrix is effected cyclically, more preferably for a time comprised between 0.01 and 10 seconds, even more preferably between 0.1 and 1 second.

Consecutive compression steps are preferably interspersed by resting steps, more preferably having a duration comprised between 0.01 and 10 seconds, even more preferably comprised between 0.1 and 1 second.

Preferably, the compression step is repeated at a constant frequency of 0.05-50 Hz, more preferably 0.5-5 Hz, most preferably 1 Hz.

Preferably, in step d) of incubating the device, the device is incubated until a three-dimensional cell and/or tissue construct is obtained, more preferably a mature tissue construct.

Preferably, step d) of incubating the device is carried out at a physiological temperature, more preferably 37° C.

Preferably, step d) of incubating the device has a duration of up to 90 days, more preferably up to 21 days, most preferably seven days.

Preferably, the device comprises an actuation chamber.

Preferably, step d) of incubating the device is preceded by a step of introduction of a fluid into the actuation chamber, preferably a liquid, and even more preferably a saline solution.

Preferably, in step d) of incubating the device, the pressure in the actuation chamber, in the compression step, is higher than the pressure in the actuation chamber in the resting step.

In a preferred embodiment, in step d) of incubating the device, the pressure in an actuation chamber, in the compression step, is comprised between 0.01 and 10 atm, more preferably between 0.1 and 1 atm, even more preferably 0.5 atm, and in the resting step it is atmospheric pressure.

In an alternative embodiment, step b) of seeding a cellular matrix comprises a step for realizing a negative pressure in the actuation chamber.

In this alternative embodiment, in step d) of incubating the device, the pressure in an actuation chamber, in the compression step, is comprised between 0 and 10 atm, more preferably comprised between 0.1 and 1 atm, even more preferably 0.5 atm, and in the resting step, it is comprised between −1 atm and −0.01 atm.

The present invention also relates to a method for testing the effect of a substance suitable for inducing a cellular response, preferably a drug, on said three-dimensional cell and/or tissue construct, which comprises the steps of putting into contact the three-dimensional cell and/or tissue construct, preferably the mature three-dimensional tissue construct, obtained according to the method of the present invention, with the substance to be tested, preferably an active ingredient of the drug, and incubating under controlled environmental conditions, more preferably at a physiological temperature, even more preferably at 37° C.

The term "substance" refers herein to a drug or active ingredient thereof, a molecule or a nanoparticle.

Preferably, the method is carried out in the device of the present invention.

Preferably, the method comprises the steps of:

making available the device of the invention containing the three-dimensional cell and/or tissue construct, preferably the mature three-dimensional tissue construct, obtained by the method for the controlled generation and/or culture and/or maturation of a three-dimensional cell and/or tissue construct at the microscale of the present invention;

introducing a suspension of the substance, preferably an active ingredient of the drug to be tested, into the compartment suitable for containing the culture medium; and incubating the device under controlled environmental conditions.

Preferably, the step of incubating the device has a duration of up to 90 days.

Preferably, the step of incubating the device is carried out at a physiological temperature, more preferably at 37° C.

The present invention also relates to the use of the device and/or method of the invention for the generation of in vitro tissue models; the pharmaceutical screening of active ingredients or drugs; the evaluation of the effects of molecules and/or nanoparticles; the modeling of rare diseases (for example genetic cardiomyopathies); or drug discovery.

Preferably, the in vitro tissue models comprise a three-dimensional cell and/or tissue construct selected from muscle, cartilage, bone, nerve, connective, fibrotic tissue, and combinations thereof, more preferably muscle tissue, even more preferably myocardial tissue, even more preferably mature.

Preferably, the drugs are selected from the group comprising cancer drugs, anti-arrhythmic drugs, adrenergic drugs, dopaminergic drugs, sympatholytic drugs and combinations thereof.

Thanks to the small dimensions involved and the optimum control of the parameters, the device and method of the present invention represent, in fact, an efficient and economical solution for the applications listed above.

Thanks to the small dimensions of the device, in fact, a smaller quantity of reagents and a limited number of cells can be used. This represents an advantage in view of the normally limited availability of cells, and of course also from an economical point of view. Furthermore, again thanks to the small dimensions and optimum performance given by the control of the parameters, the device of the invention allows satisfactory results to be obtained in relatively short periods of time.

It has been surprisingly found, in fact, that, thanks to the exact control on the compression of the cell construct (and in any case the cellular matrix), optionally repeated in time, and at the same time the efficient perfusion of the culture medium inside the construct itself, it is possible to obtain in an optimal way the differentiation of cells and generation of a mature tissue construct, which is repeatable, rapid and reliable, at the microscale.

Thanks to the physical characteristics of the confinement means, an optimum perfusion of the culture medium through the whole cellular matrix can be obtained, also reaching the innermost cells of the cellular matrix.

This aspect is further improved by the very dimensions of the device which allow optimal volume/surface ratios for the performance. The culture medium, at the microscale, can in fact reach the innermost cells of the cell construct even more easily. There is therefore a homogeneous behaviour of the cells inside the cell construct. This represents a greater control element with respect to devices on a larger scale.

As already mentioned above, it should also be noted that the above physical characteristics of the confinement means, such as, for example, their hydrophobicity, allow the surface tension characteristics of the cellular matrix to be best exploited for the very confinement of the cellular matrix, in particular when this is in the form of a fluid solution. This effect, which is obtained at the microscale, does not occur on a larger scale.

This control can be further improved by various factors.

The confinement means, in particular the micropillars, are positioned so as to create a certain distance with respect to the counter element (at rest) and can therefore represent a "run-end" element of the movement of the counter element.

Exerting a compression which gives rise to a uniaxial extension rather than a biaxial extension, for example, with the creation of microfluidic channels having a length that is the same as that of the culture chamber itself, allows a greater predictability of the behaviour of the cellular matrix subjected to compression. It is thus within the abilities of a person skilled in the field to calibrate the compression exerted on the cellular matrix on the basis of the result to be obtained.

The device and method of the present invention are particularly useful in optimizing differentiation protocols of induced pluripotent stem cells (IPS) in cardiomyocytes and engineering strategies of heart tissue.

In a preferred embodiment, the invention envisages the presence of various microfluidic channels in parallel, positioned so that the cellular matrices between them are not in reciprocal contact. This embodiment allows a plurality of tests to be carried out in parallel, further improving the efficiency of use of the device and method of the invention. In particular, with respect to the above tests in parallel, the cell constructs can be subjected to the same stimulation conditions.

This aspect is advantageous when it is important to replicate identical conditions on the same system or on different systems. Alternatively, the device can be realized for allowing the application of different conditions in the cell constructs of the single microfluidic channels, for example creating chambers with different geometries.

Furthermore, the same microfluidic channel can be divided into various microfluidic channels in series, in order to increase the number of cell constructs within each device, which can be obtained without significantly increasing the number of cells used. This makes the device "high-throughput".

This also enables the seeding of cell monolayers in contact with and in addition to the cell construct of the invention.

The device of the invention is easy to manufacture as it is obtained with conventional microfabrication techniques, such as photo- and soft-lithography.

Furthermore, thanks to its small dimensions and ease of manufacture, the device, as also the method, of the invention is economical.

The method and device of the invention allow the construction of three-dimensional in vitro models based on cells, even human cells. Thanks to the reduced dimensions involved, in fact, the present invention overcomes the drawbacks relating to the availability of human cells typical of the known art and therefore enables the provision of a human model when the known art must resort to animal cells. This results in a model which, at low costs, allows tests to be carried out in vitro directly on mature tissue constructs obtained from human cells, thus obtaining more predictive results of the in vivo situation.

In particular, and with reference to all of the advantages indicated above, the device and method of the present invention allow three-dimensional tissue constructs to be cultivated at the microscale, of a patient (human) from cells, for example, stem cells of the same, thus providing constructs which are particularly useful in clinical settings.

Unlike the methods and devices of the known art, in the method and device of the present invention, it is not necessary to impart an electrical stimulus for obtaining a mature tissue construct. The device of the invention, however, can be provided with housings for the insertion of electrodes in the device. In this way, an electrical stimulation can be imparted to the cell construct in addition to mechanical stimulus.

This embodiment is particularly useful for imparting a pacing in cardiac constructs.

DETAILED DESCRIPTION OF THE INVENTION

Figure 1:
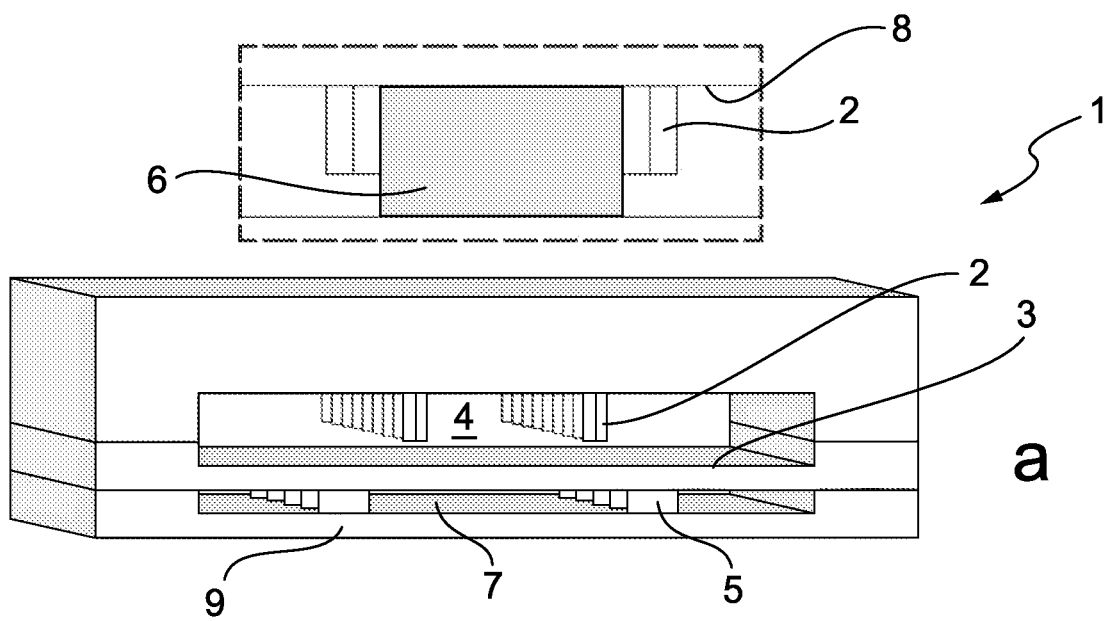
FIG. 1 shows a schematic representation of the device according to a preferred embodiment of the present invention in a resting position (a) and a compression position (b).
Figure 1:
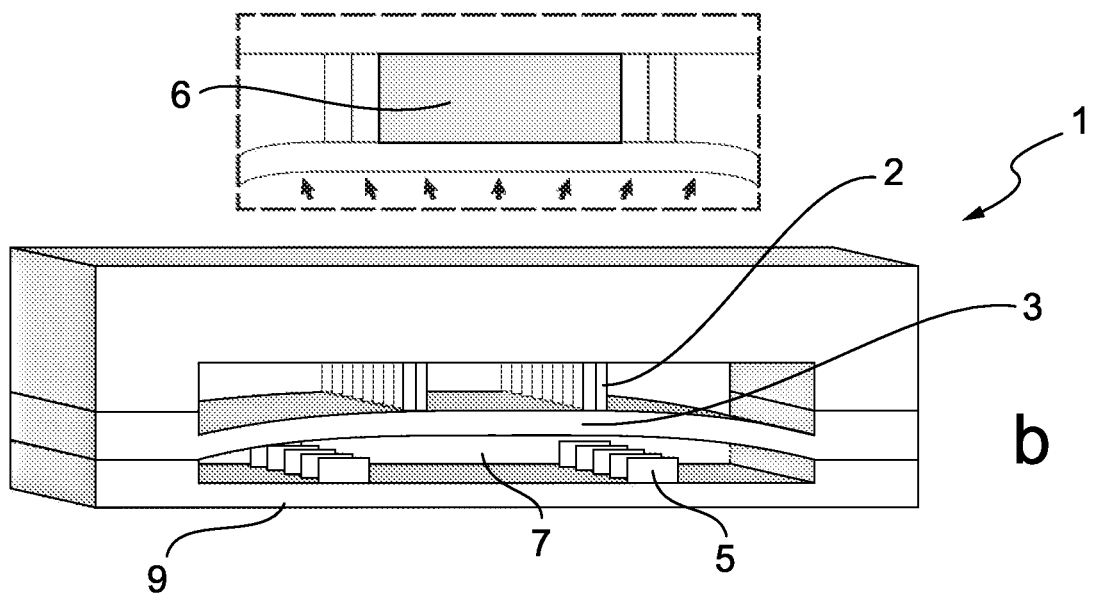

With reference to the figures, in particular FIG. 1, according to a preferred embodiment of the present invention, the microfluidic device, indicated as a whole with the numeral 1, is composed of a culture chamber 4 and an actuation chamber 7 below the culture chamber.

The confinement means 2 are situated, in this embodiment, on the upper wall 8 of the culture chamber 4 and consist of a series of micropillars (in this case, the micropillars are prisms with an hexagonal cross section) positioned in two parallel rows between each other so as to form a microfluidic channel, that is rectangular-shaped. The perimeter of the microfluidic channel is therefore defined, on two opposite sides, by the two parallel rows of micropillars 2 and on the remaining opposite sides by the walls of the same culture chamber itself (not shown herein).

In other embodiments, the micropillars can be positioned so as to have any other geometrical form. It is not necessary that the walls of the culture chamber form two of the opposite walls that define the perimeter of the cellular matrix, as the micropillars can define the whole perimeter of the polymeric matrix. For a better control of the compression, it is preferable for the perimeter to define a regular geometrical form, for example, a circumference, a square, a hexagon, etc.

In other embodiments, the micropillars can be positioned so as to form a plurality of microfluidic channels, for example parallel or in series with respect to each other, functionally isolated from each other.

In this way, in fact, in the application of the device for the development, for example, of a drug, various tests can be carried out in parallel, thus optimizing the time-scale and the space required, in addition to the reliability of the same test.

According to a further embodiment of the invention, the confinement means 2 can be produced so as to be suitable for containing various layers of cellular matrices, in order to form composite cellular matrices. This further embodiment can be implemented, for example, by the introduction of one or more additional layers of cell culture overlying (or underlying) the main layer, and separated from the adjacent layers by means of a pervious membrane.

It is not essential that the microfluidic channel is positioned centrally with respect to the width of the upper wall 8. This however is the preferred embodiment as it allows an even perfusion of the culture medium (CM) on the two sides.

The confinement means, in particular the micropillars, are preferably made of a hydrophobic material, for example silicon rubber, for example polydimethylsiloxane (PDMS), fluorinated rubber, polystyrene (PS), and combinations thereof, more preferably silicon rubber.

Such means can also be made of another material, such as, for example, polymethyl methacrylate (PMMA), polycarbonate (PC), polyethyleneglycol (PEG), glass, silicon, and combinations thereof, and be provided with a hydrophobic nature, for example by means of chemical and/or physical surface treatment.

It is important for the confinement means 2 to have hydrophobic or low hydrophilicity characteristics, as the device of the present invention exploits the surface tension characteristics of the cellular matrix, in particular when it is introduced in liquid or fluid form into the compartment suitable for containing the cellular matrix. This allows the cellular matrix to be confined within the perimeter defined by the confinement means, in this case micropillars, and within the thickness delimited by the proportions between the height of the confinement means and the height of the culture chamber, and at the same time an efficient cell culture is obtained thanks to the passage of the culture medium (CM) through the spaces separating adjacent micropillars.

Furthermore, as explained in greater detail hereunder with reference to FIG. 1*b*, the spaces between adjacent micropillars allow the cellular matrix to extend during the compression step, occupying the above spaces, in the compression position.

The confinement means, in particular the micropillars, therefore exert four functions: they contain the cellular matrix, they allow the extension of the cellular matrix, they allow the passage of the culture medium, and they possibly also act as a run-end for stopping the counter element (which will be discussed in further detail hereunder).

In order to obtain the desired result through the device of the invention, in fact, it is essential that the culture medium be able to optimally reach all the culture cells, even the innermost cells in the cellular matrix.

This aspect becomes particularly important as the cell culture becomes gradually transformed into a three-dimensional tissue construct, more preferably mature, wherein there are possibly a larger number of cells and which are more compact.

In the specific case of micropillars, if, on the one hand, it is advantageous to have a relatively large distance between adjacent micropillars for the reasons indicated above, said distance must, however, be sufficiently small as to allow the surface tension characteristics of the cellular matrix to be exploited during its injection into the device, in order to be able to confine the cellular matrix.

In this embodiment represented in FIG. 1, the counter element 3 is the lower wall of the culture chamber 4.

Other solutions are of course possible, such as, for example, the fact that the counter element can form only a part of the wall.

In a preferred embodiment, the counter element has a behaviour which includes an elastic component, in particular it is a flexible membrane.

In a preferred embodiment, the counter element 3, or the flexible membrane, is made of silicon rubber (for example polydimethylsiloxane (PDMS), but fluorinated rubber, polystyrene (PS), polymethyl methacrylate (PMMA), polycarbonate (PC), glass, silicon, polyethyleneglycol (PEG), and combinations thereof, are equally valid.

In the embodiment of FIG. 1, it can be seen that the cellular matrix 6 rests on the counter element 3 in the resting position without undergoing compression.

In the same way, the cellular matrix can be in contact with the counter element and can additionally be subjected to compression, which however is always lower than that at which the same is subjected when in a compression position.

The cellular matrix may also not be in contact with the counter element in a resting position (embodiment not shown).

In the embodiment shown in FIG. 1, the actuation chamber 7 has the function of generating a mechanical stimulus suitable for causing the movement of the membrane 3 in the direction of the cellular matrix 6, compressing it.

Other embodiments can of course also envisage different relative positions of the various elements, wherein, for example, the confinement means are on the lower wall of the culture chamber and the counter element is on the upper wall, and the actuation chamber is above the culture chamber.

As mentioned above, the actuation chamber is not essential, as the compression step of the cellular matrix can be realized with other expedients known to skilled person in the field (actuation of the type chosen from the pneumatic, hydraulic, mechanical, electrical, magnetic, thermal types, and combinations thereof). A piston mechanical actuation can be used, for example, or an electromechanical actuation using a piezoelectric element.

Furthermore, the mechanical stimulus does not have to be created by the counter element 3, as it is also possible for the wall comprising the confinement means 8 to undergo a movement towards the counter element 3 which is stationary.

Similarly, both the wall comprising the confinement means 2 and the counter element 3 can undergo movement towards each other.

In order to obtain the compression of the cellular matrix in the compression step, the confinement means and the at least one counter element must in fact undergo a movement of at least one of these towards each other.

In the embodiment shown in FIG. 1, the actuation chamber 7 comprises, on its upper wall, the counter element 3, in particular a flexible membrane.

Preferably, supporting means 5, for example two rows of micropillars, are positioned between the counter element and the lower wall 9 of the actuation chamber 7, whose function is to support the membrane when the device is in the resting position. Their presence, however, is not compulsory.

The actuation chamber 7 can comprise a saline solution in its interior.

In order to generate the movement of the membrane 3 towards the cellular matrix, the interior of the actuation chamber 7 is subjected to a pressure increase which leads to the upward flexion or deflection of the membrane 3 which thus compresses the cellular matrix (as illustrated in FIG. 1*b*).

In a preferred embodiment, the pressure inside the actuation chamber 3 in resting position (FIG. 1*a*) is atmospheric pressure and in order to generate the movement of the membrane 3 towards the cellular matrix, the interior of the actuation chamber 7 is subjected to a positive pressure which causes the upward flexion of the membrane 3 which thus compresses the cellular matrix.

In an alternative embodiment (shown in FIG. 6), the pressure inside the actuation chamber 3 in resting position (a) is negative and in order to generate the movement of the membrane 3 towards the cellular matrix, the interior of the actuation chamber 7 is subjected to a pressure increase which causes the upward deflection of the membrane 3 which thus compresses the cellular matrix in compression position (b).

The width of the counter element is preferably sufficiently high so that the flexion induced by its activation results in a low curvature in the central part, so that the cellular matrix perceives this flexion mainly as a shifting of the counter element, thus creating a substantially homogeneous compression of the cellular matrix with respect to the whole of its surface in contact with the counter element.

Thanks to the controlled pressure regulation, a controlled compression can be exerted on the cellular matrix, which can be regulated according to requirements. Alternatively, as shown in FIG. 1b, the compression control can be accurately obtained with the use of the confinement means as run-end for the counter element. In this way, the regulation of the compression can be obtained by controlling the relative geometric ratios (height of the confinement means, distance between the confinement means and the counter element and the distance between the same confinement means).

The quantity of pressure applied and its application frequency depend on the cell culture and the type of construct to be formed.

In a preferred embodiment, the construct to be obtained is a beating myocardial tissue construct and consequently, after introducing cardiac cells into the device, pressure is exerted cyclically with a frequency of about 1 Hz, as explained in greater detail hereunder.

As shown in FIG. 1b, the upward bending of the membrane in a compression position leads to the compression of the cellular matrix which consequently extends in the direction of the width of the microfluidic channel, i.e. causing a uniaxial extension. As already mentioned, in fact, as two opposite ends are delimited by the very walls of the culture chamber, it is not possible for the cellular matrix to extend in the direction of the length.

As indicated above, there is a possible embodiment in which the microfluidic channel is not delimited by the walls of the culture chamber in the direction of the length but, on the contrary, it is delimited by a further two rows of micropillars. In this case, there is a biaxial extension of the cellular matrix.

The extension of the cellular matrix in the direction of the width of the microfluidic channel is enabled by the spaces present between adjacent micropillars.

Figure 2:
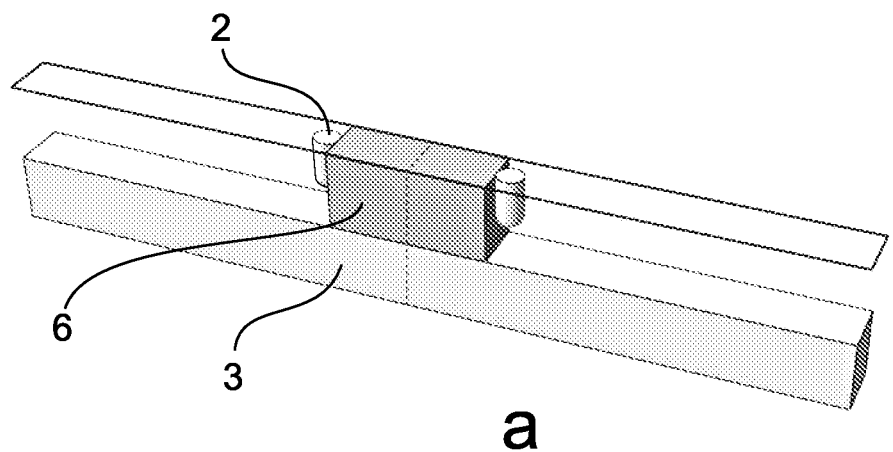
FIG. 2 shows a schematic representation of a detail of the culture chamber of a device according to a preferred embodiment of the present invention in a resting position (a) and a compression position (b).
Figure 2:
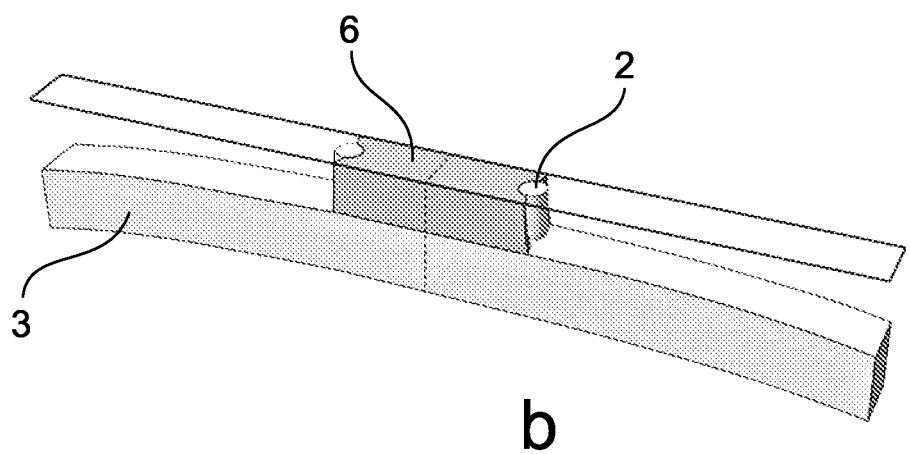

As can be seen from FIG. 2, in fact, which shows a schematic representation of a detail of the culture chamber, according to a preferred embodiment, in resting position (a) and in compression position (b), with particular reference to the resting step, the cellular matrix 6 rests on the flexible membrane 3. The micropillars 2 are adjacent to the cellular matrix on two of its opposite sides. There is no mechanical stimulus.

In the compression position (b), the membrane 3 bends upwards thus compressing the cellular matrix which in turn extends along the direction of the width of the microfluidic channel, thus slipping into the spaces between adjacent micropillars (not shown). It can be seen from FIG. 2b that the thickness of the cellular matrix 6 is reduced with respect to FIG. 2a and, at the same time, the width is increased, thus occupying the areas around the micropillars 2 which, in FIG. 2a, were free.

The compression exerted on the cellular matrix is controlled, i.e. it is of a known entity, as it can be regulated as desired by a skilled person in the field, and is reproducible. This feature is obtained, for example, thanks to the action of the actuation chamber which allows a well-defined pressure to be exerted in its interior, which in turn results in a well-defined compression on the cellular matrix. Furthermore, thanks to the geometrical regularity characterizing the positioning of the micropillars, and the homogeneity of the distances between adjacent micropillars, the extension of the cellular matrix takes place uniformly along the whole length of the microfluidic channel. Finally, the fact that, according to the preferred embodiment represented in FIG. 1 and in FIG. 2, the microfluidic channel is delimited on two opposite walls by the walls of the culture chamber itself, means that the extension can take place in only one direction, and is therefore mainly uniaxial.

The compression of the cellular matrix causes a reduction in the thickness of the cellular matrix comprised between 1 and 90% with respect to the thickness of the same in resting position and/or in resting step and/or before the compression step, more preferably comprised between 15 and 50%, even more preferably about 35%.

The extension of a dimension of the cellular matrix in compression position (or step) is preferably comprised between 1 and 100% with respect to the same dimension of the cellular matrix in resting position (or step) and/or before the compression step, more preferably comprised between 5 and 20%, even more preferably about 10%.

On the basis of the result to be obtained, a skilled person in the field is able to select the optimal compression degree.

In the same way, the minimum distance between the confinement means and the counter element can be selected so that it is as optimal as possible on the basis of the result to be obtained. In the compression position, in fact, the micropillars can form run-end elements of the counter element, as already mentioned above. In other words, when, in the compression position, the counter element and the confinement means come into abutment with each other, this defines the maximum compression of the cellular matrix that can be obtained in that device. By suitably selecting the reciprocal distances between the confinement means and the counter element, and also the thickness of the polymeric matrix, the desired reproducible compression can therefore be reliably obtained.

A skilled person in the field is naturally able to calibrate the minimum distance between the confinement means and the counter element, the thickness of the cellular matrix and the distance between adjacent micropillars and between rows of micropillars, for obtaining the desired result.

Once the compression has been exerted on the cellular matrix, in the compression step, the device is then restored to resting position, exploiting the elastic recoil of the material of the counter element. Analogously, thanks to its behaviour which includes an elastic component, the cellular matrix tends to return to its original thickness once restored to resting position.

If bent during the compression step, the confinement means also return to their original resting position. The duration of the compression, in the compression step, is extremely variable. For the generation of certain three-dimensional cell and/or tissue constructs, a compression can in fact be applied that has a duration even up to the completion of the generation of a mature tissue construct, therefore requiring a few days.

The duration of a compression step preferably ranges from 0.01 to 10 seconds, more preferably from 0.1 to 1 second.

In the compression step, the compression can be applied once only, or it can be repeated multiple times.

Even more preferably, the compression step is carried out cyclically interspersed by a resting step (or position) which is maintained for a time comprised between 0.01 and 10 seconds, more preferably between 0.1 and 1 second.

Even more preferably, the compression step is carried out cyclically with a frequency comprised between 0.05 and 50 Hz, more preferably comprised between 0.5 and 5 Hz, most preferably about 1 Hz.

Figure 3A:
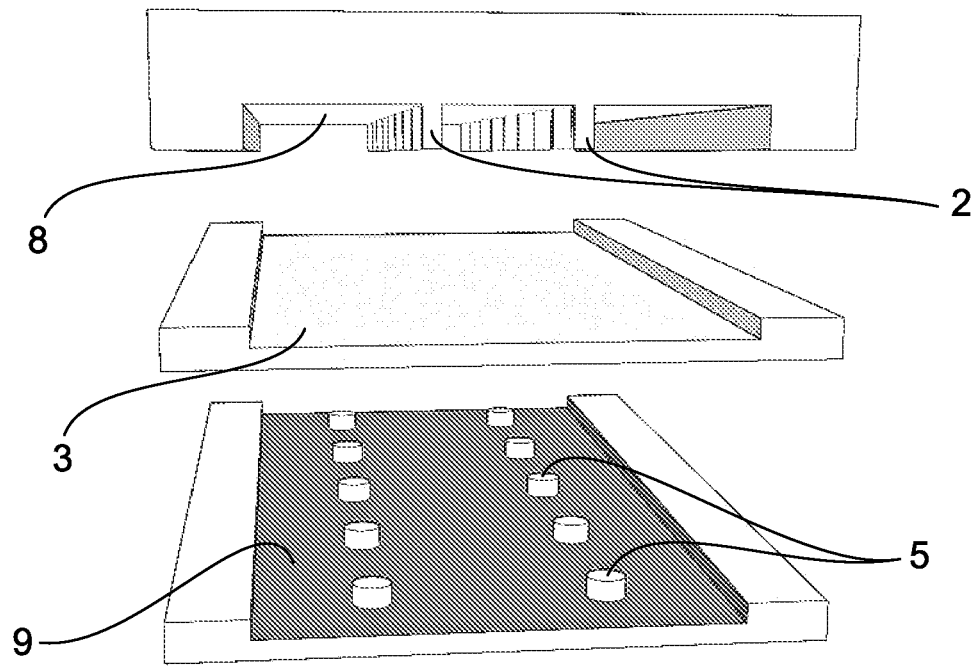
FIG. 3 shows an exploded view of the device of the invention according to a preferred embodiment (FIG. 3*a*) and a representation, according to a preferred embodiment of the present invention (FIG. 3*b*), of the culture chamber and actuation chamber and their respective inlet and outlet openings for the cells and for the culture medium.

FIG. 3a illustrates an exploded view of the device of the invention according to a preferred embodiment and shows the three main parts forming it: the upper wall 8 associated with the confinement means 2 in the form of micropillars; the wall comprising the counter element 3; and the lower wall 9 of the actuation chamber 7, also associated with supporting means 5, in the form of micropillars.

Figure 3B:
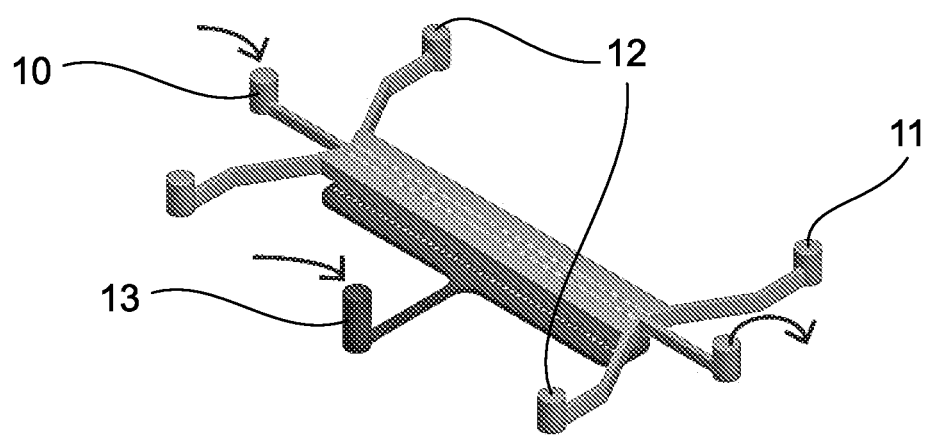

FIG. 3b shows a representation of the culture chamber and actuation chamber and their respective inlet 10 and outlet 11 openings for the cellular matrix and inlet and outlet for the culture medium 12. The inlet of the pressure line 13 is also shown.

It is evident that whereas the inlets and outlets for the cellular matrix 10, 11 and for the culture medium 12 are compulsory, the inlet of the pressure line 13 is optional, depending on the embodiment to be implemented.

It should be noted that the number of inlets and outlets shown in the figure is not compulsory, but the number of the above can vary as desired.

Furthermore, it is not compulsory to provide housings for electrodes. The electrodes can in any case be inserted directly inside the access gates already present (for example, the wells for the inlet and outlet of the culture medium).

Figure 4:
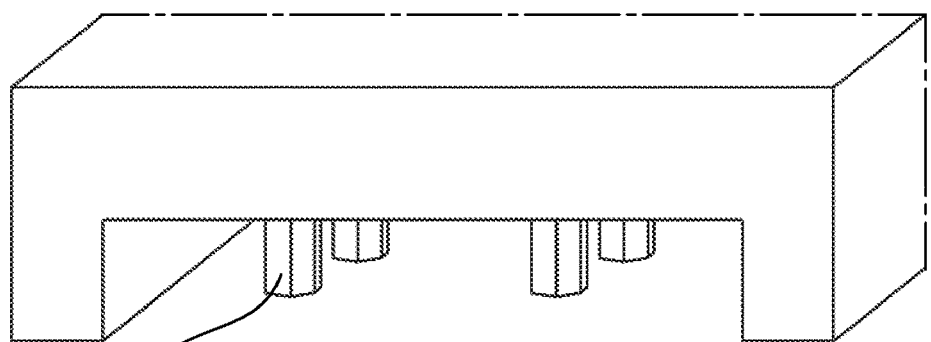
FIG. 4 shows a schematic representation of the parts (a-c) that compose the device of the invention according to a preferred embodiment.
Figure 4:
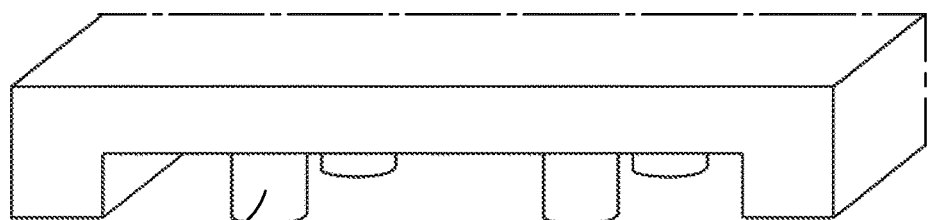
Figure 4:
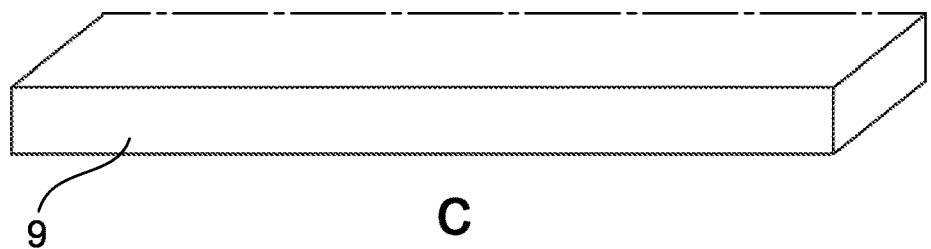

In the production of the device of the invention through microfabrication techniques, for example lithographic techniques, various parts can be produced separately, which are subsequently joined together according to techniques known in the field for forming the device of the invention. There can be three of these parts corresponding to those illustrated in FIG. 3a. Alternatively, two parts can be obtained with microfabrication techniques, as illustrated in FIG. 4, in which the two parts (a,b) above, which together define the culture chamber and part of the actuation chamber, are produced with the above techniques, whereas the lower part (c) can be produced with different techniques, as it is a simple plane which will form the floor of the actuation chamber.

Figure 5:
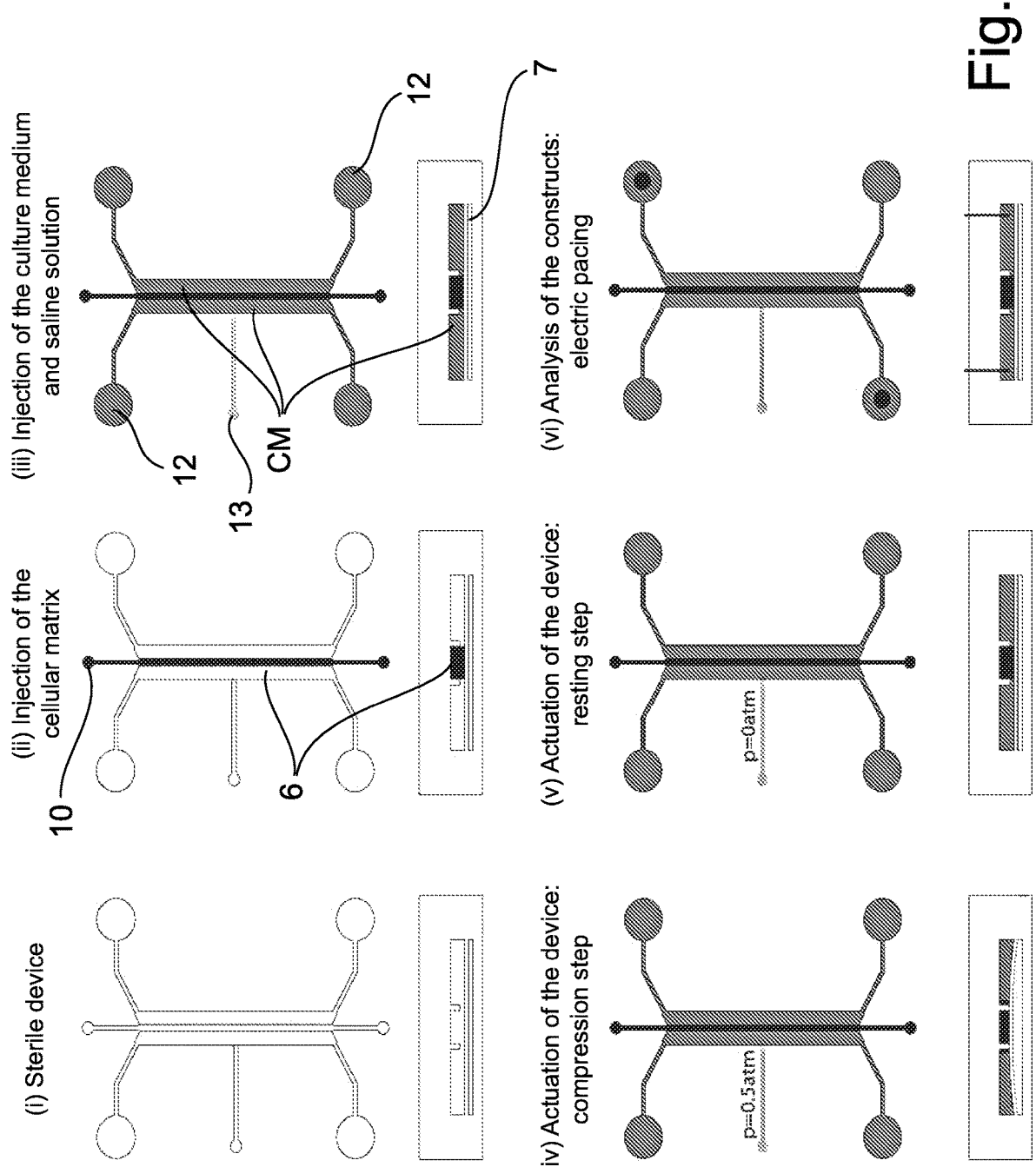
FIG. 5 shows a representation of the device when functioning according to a preferred embodiment of the invention illustrated through the sequence of steps (i) to (vi).

With reference now to FIG. 5, the method of the present invention is described hereunder according to a preferred embodiment, in its various steps represented by numbers (i) to (vi) for the formation of a three-dimensional cardiac tissue construct. According to a preferred embodiment, therefore, as represented in FIG. 5(i), the device of the invention is provided according to a preferred embodiment which corresponds to that represented in FIG. 1. The device is previously sterilized and a quantity of cellular matrix is inserted in its interior through the opening for the cellular matrix 10, which is sufficient for occupying the specific microfluidic channel (FIG. 5(ii)). This corresponds to a quantity of about 0.5 µl. This quantity is naturally variable depending on the volume to be occupied by the cellular matrix.

The cellular matrix preferably comprises a polymer, in particular fibrin and is in fluid form. The isolation of the cells, for example cardiac cells extracted from hearts of neonatal rats to be seeded, and their treatment before mixing with the polymer and their introduction into the microfluidic device is effected according to procedures known and consolidated in the field, described in detail in the Examples.

As explained above, other types of cells which are equally suitable for forming three-dimensional cell and/or tissue constructs, preferably mature three-dimensional tissue constructs can of course be used with the device of the present invention.

The polymers that can be adopted in the cellular matrix can be in the liquid or semi-solid state to enable them to be injected into the device and be capable of polymerizing after injection to form a gel.

Aggregates of cells can also be injected into the device in a small amount of a fluid (normally the culture medium), in the absence of a polymer. The possible presence of natural polymers generated by the cells themselves can in fact be sufficient for providing the cellular matrix thus formed, with the elastic characteristics necessary for the proper functioning of the method and device of the present invention.

The concentration of the cardiac cells in the cellular matrix is preferably $1\times10^5$ cells/µl. This concentration can naturally vary in relation to the cells involved and the type of cell construct desired from $1\times10^2$ to $1\times10^6$ cells/µl.

The device is then incubated at 37° C. for 5 minutes to allow the cellular matrix to polymerize. At this point, the cellular matrix is in the form of a semisolid gel (cell construct), in particular, as represented in FIG. 5(ii), in the form of a microfluidic channel.

The polymerization conditions can naturally vary in relation to the materials used.

The culture medium (liquid) is then injected, as shown in FIG. 5(iii) through one of the inlets 12 and goes into the culture chamber in the compartments suitable for containing the culture medium (CM). In this way, in practice, and if the volume of culture medium allows this, the culture medium occupies the whole space remaining available in the culture chamber upon polymerization of the cellular matrix.

Thanks to the spaces between the micropillars, the medium is in contact with the cellular matrix in many points along the length of the microfluidic channel thus being able to efficiently feed the cells of the cellular matrix.

A fluid is then introduced into the actuation chamber 7 by means of the pressure line 13.

Figure 6:
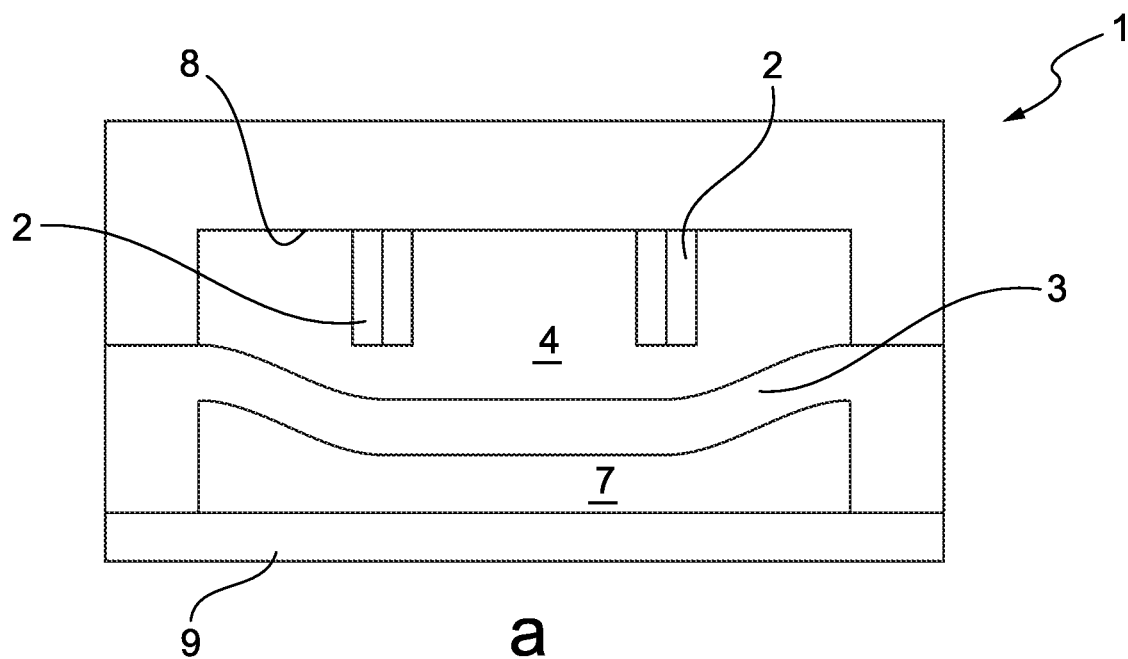
FIG. 6 shows the device of the invention in an alternative embodiment of the invention in a resting position (a) and a compression position (b).
Figure 6:
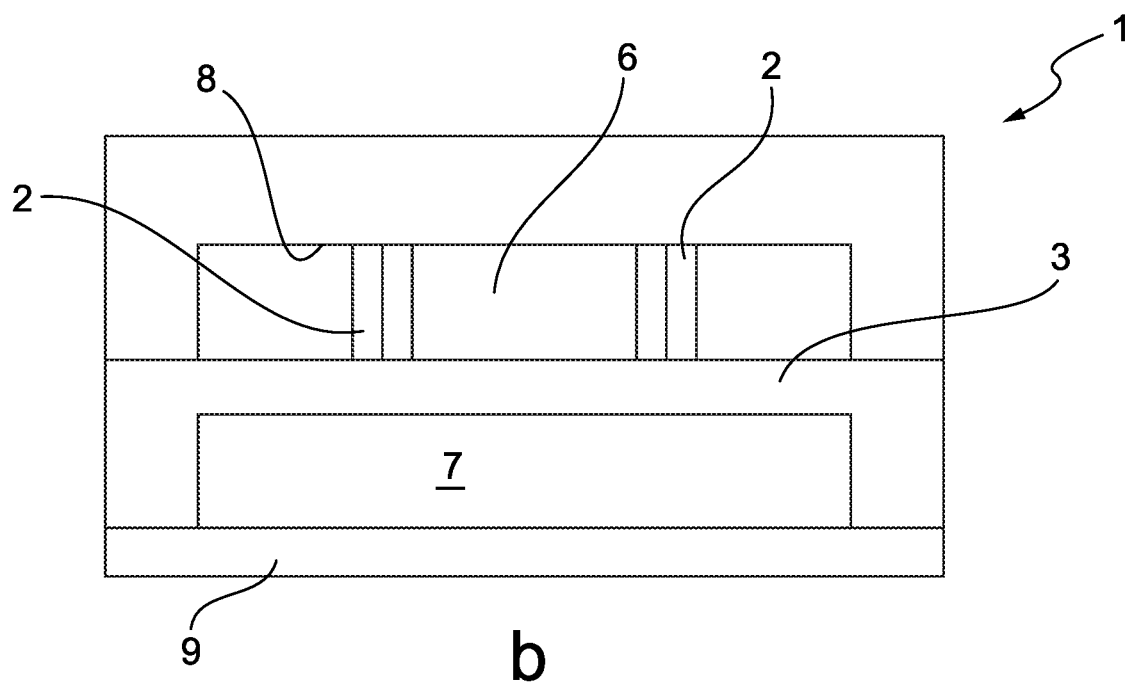

In the embodiment represented in FIG. 6, a negative pressure is created inside the actuation chamber, with the expulsion of air from the actuation chamber, so as to cause a downward flexion of the counter element. The air to be expelled can be air previously and specifically introduced.

After creating a negative pressure, the cellular matrix is introduced and goes onto the supporting element (in this case a membrane).

In this embodiment, the compression of the cellular matrix is obtained with an increase in the pressure inside the actuation chamber, which causes an upward deflection of the membrane.

The device thus prepared, according to FIG. 5, is then incubated at a temperature of 37° C. for 7 days with the application of a pressure at the inlet 13 of 0.5 atm at a frequency of 1 Hz.

Although the above parameters are variable, it is clearly not possible to deviate much from the physiological temperature of 37° C. in order to have the best results, as this corresponds to the temperature of a healthy human body.

If the tissue construct to be generated is of an animal origin, whose healthy body temperature is different from 37° C., the incubation temperature can naturally be adjusted to the temperature of the healthy body of the animal in question.

The pressure is regulated, as shown in FIGS. 5(iv) and 5(v), to 0.5 atm by a precision pressure regulator, and the cyclic stimulus is obtained, for example, by means of an electronically controlled electrovalve destined for alternating the pressure in the actuation chamber between environmental pressure to an overpressure of 0.5 atm.

The frequency of the compression step is variable depending on the type of cells used.

As shown in FIG. 5(iv), the confinement means and the counter element 3 (in this case a membrane) are in a compression position, wherein the membrane is flexed towards the micropillars 2, whereas in FIG. 5(v), they are in a resting position, and there is no mechanical stimulus.

During the incubation period, it may be necessary to substitute the culture medium (CM), which is changed through the access openings 12.

A fresh culture medium can be introduced still through the inlets 12 at a desired time of the incubation period.

During the incubation period, it can be observed that the cellular matrix, initially consisting of cells separate from each other, is transformed into a more compact three-dimensional construct in which the cells are functionally bound to each other and capable of responding to stimuli as a syncytium. In particular, the three-dimensional cell construct has movements of contraction and relaxation, in which the cells have a synchronous behaviour with respect to each other, until the formation of a mature tissue construct.

With reference to FIG. 5(vi), this figure illustrates a possible method for performing electrical pacing analysis of a mature beating cardiac three-dimensional tissue construct in synchronous contraction, generated according to the method of the present invention.

As mentioned above, in fact, although the method of the present invention does not require electrical stimuli for its functioning, the latter can be used once a mature cardiac construct has been obtained, for example, at first to verify that a beating construct has been obtained, and subsequently to impose a certain beating pace. A construct thus regulated is particularly useful in those tests which imply the heart as target organ.

In this respect, it should be noted that this latter aspect can only be applied to muscle constructs and not to other types of constructs (for example bone or cartilage).

In order to carry out tests on a substance, preferably a drug or active ingredient, a molecule or a nanoparticle, using the construct obtained with the method of the invention, the device of the invention is preferably used. At the end of the generation of a mature three-dimensional tissue construct inside the device of the invention, the substance to be tested can in fact be introduced directly into the culture medium, for example in the form of a solution.

The amount or concentration of the substance to be tested, as well as other experimental factors such as the temperature and duration of the incubation of the device, is naturally variable and depends on numerous factors known to skilled persons in the field.

The present invention is now further illustrated by means of embodiment examples as provided hereunder.

Example 1

Description of the Device

A multilayer microfluidic device in silicon polydimethylsiloxane (PDMS) was manufactured. The device obtained is composed of two compartments separated by means of a membrane (counter element): an upper chamber (culture chamber, dimensions: 1600 µm in width, 3 mm in length and 150 µm in height), for obtaining three-dimensional tissue constructs, and a lower chamber (actuation chamber), used for providing the cyclic mechanical stimulation, by means of pneumatic actuation. The culture chamber (height 150 µm) consists of a central microfluidic channel having a width of 300 µm delimited by two rows of hexagonal micropillars (height 100 µm, side 28 µm), wherein adjacent micropillars are equidistant from each other (by 50 µm). The micropillars were produced attached only to the upper wall of the compartment, so as to be left suspended and separated from the membrane (which represents the floor of the culture chamber) at a distance of 50 µm. The central channel is surrounded by two side channels (width 600 µm each), dedicated to containing and transporting the culture medium for feeding the cells.

Construction of the Device

The device previously defined was manufactured with the use of photo- and soft-lithographic techniques. The layout of the device was produced through computer aided design (CAD) and is composed of three layers (see FIG. 3a): the first two layers that form the culture chamber, respectively 100 µm (layer containing the micropillars) and 50 µm in height (confinement tank that defines the minimum distance between the micropillars and floor of the culture chamber); and the third layer containing the mechanical actuation chamber, 50 µm in height. The layout of each layer was printed at high resolution (32,000 dpi) on a photomask and subsequently transferred onto a silicon wafer by means of photolithography. For each layer, a film of photosensitive polymer (fotoresist negative, SU-8 2050), having a thickness equal to the design-based height of said layer, was deposited on a silicon wafer having a diameter of 4" (about 10 cm). Said film was then exposed to collimated ultraviolet light (λ=365 nm), filtered by the corresponding photomask, so as to induce the crosslinking of the polymer in correspondence with the exposed areas alone. Once the excess of non-polymerized photoresist had been eliminated, the three microstructured silicon wafers obtained (i.e. having the layouts of the layers in bas-relief) were used as moulds for obtaining three blocks of PDMS. In particular, a solution of PDMS in liquid phase was prepared by mixing its two components, pre-polymer and crosslinking agent, in a ratio of 10:1 and put under vacuum for at least 15 minutes, so as to eliminate the presence of residual air. The solution was then poured onto the moulds and left to crosslink at 65° C. for 3 hours. The volume of PDMS to be poured onto each mould was established so as to obtain the desired height of the block: more specifically, 5 mm on the mould containing the micropillars, 300 µm on the mould of the confinement tank and 300 µm on the mould of the actuation chamber. The inlets to the various compartments were obtained by perforating the PDMS blocks with biopsy punchers having adequate dimensions in correspondence with the access channels designed. In particular, two inlets were produced, having a diameter of 500 µm for the injection of the cellular matrix, an inlet having a diameter of 500 µm for the pressurizing of the actuation, 4 inlets having a diameter of 5 mm for the injection of the culture medium. Finally, the assembly of the device was effected by chemically gluing the three blocks of PDMS, after alignment, and after plasma activation treatment.

Example 2

Preparation of the Device

The device thus obtained in Example 1 was sterilized by means of an autoclave (20 minute cycle, temperature of 120° C. and pressure of 2 bar) and left in an oven at 80° C. for 24 hours to restore the natural hydrophobicity of the PDMS. The device was then used for the generation and maturation of 3D cardiac constructs, produced by charging a solution of fibrin hydrogel with cardiac cells extracted from hearts of neonatal rats. Before use, the actuation chamber was completely filled (1 µl) with a buffer solution (saline phosphate buffer, or PBS 1×). More specifically, the actuation chamber was connected to a flexible rubber tube (internal diameter 0.5 mm), half filled with PBS and half with air, to a compressed air line through a pressure regulator. A constant pressure of 0.3 atm was applied for the filling of the actuation chamber with PBS, for 45 minutes, so as to impose the outflow of air contained in the chamber through the same walls of PDMS and its substitution with PBS.

Preparation of the Cells

The cells of interest were isolated using the following process. The cardiac tissue removed from the ventricles of neonatal rats was digested in trypsin (0.6 mg/ml, in a Hank balanced saline solution, HBSS) for 18 hours. The digestion was then blocked by adding 10 ml of culture medium (Dulbecco Modified Eagle's Medium, DMEM) containing: 10% of fetal bovine serum, 1% of penicillin-streptomycin, 1% of HEPES and 1% of L-Glutamine. The isolation of the cells from the matrix was then obtained with five passages in a solution of collagenase (1 mg/ml in HBSS) at 37° C. for 5 minutes. The cell suspension thus obtained was centrifuged at 700 rpm for 10 minutes, re-suspended in 25 ml of culture medium and seeded in a culture flask to isolate the fraction of cardiomyocytes (non-adherent).

After an hour, the fraction of non-adhering cells (consisting of about 85% of cardiomyocytes and 15% of cardiac fibroblasts, was collected and centrifuged at 1,200 rpm for 5 minutes, in order to estimate the number of cells obtained.

Generation of the Mature Cardiac Tissue Construct

For seeding inside the device, the cardiac cells thus isolated were diluted in a solution of fibrin gel at a cell concentration of $1 \times 10^5$ cells/µl. More specifically, for the seeding of 6 devices, 20 µl of fibrin gel were prepared by mixing $20 \times 10^5$ cells (estimated volume of 8.2 µl), 4 µl of calcium chloride, 4 µl of fibrinogen (20 mg/ml in sodium chloride), 2.8 µl of aprotinin (16 TIU/ml in distilled water) and 1 µl of thrombin (5 U/ml in calcium chloride). The solution composed of fibrin gel and cells was sucked by means of a 1 ml syringe into a flexible rubber tube (internal diameter of 0.5) terminating with a metallic tube (standard measurement 23 G and length 12.5 mm). The cell seeding in each device was effected by directly inserting the metallic terminal tube into the inlet of the device destined for the injection of the cellular matrix, and injecting a volume of 0.5 µl of solution, by activating the plunger of the syringe, into the central channel of the culture chamber. In order to obtain a complete polymerization of the fibrin gel, the devices were inserted in an environmental incubator (T=37° C., $CO_2$=5%) for 5 minutes and a culture medium containing a fraction of aprotinin (1.15 TIU/ml) was subsequently injected into the side channels, until the 4 compartments for the culture medium had been completely filled (aprotinin inhibits the digestion of the fibrin gel on the part of the cells). The culture medium was changed manually once a day during the whole incubation period (7 days). Immediately after the polymerization of the fibrin gel, the cell constructs were subjected to cyclic uniaxial mechanical stimulation (extension of the dimension of the width of the microfluidic channel equal to about 10%, frequency 1 Hz), obtained by pressurizing the saline solution contained in the actuation chamber, through an electronically controlled electrovalve (destined for alternating the pressure in the chamber between atmospheric pressure and an overpressure of 0.5 atm).

Example 3

Analysis of the Constructs: Stains

The effect of the cyclic mechanical stimulation on the maturation of the 3D cardiac tissue constructs was analyzed and the results were compared with those obtained in analogous non-stimulated devices used as negative controls. In particular, the effect of the mechanical stimulation on the cell viability was evaluated after 3 days by means of LIVE/DEAD assay showing a statistically lower mortality in the presence of cyclic mechanical stimulation. More specifically, 85.39%±0.58% of viable cells were quantified in the mechanically stimulated cell constructs with respect to 66.87%±1.84% in the non-stimulated control constructs, after three days of culture. The morphology, organization, maturation, and formation of synergic structures between the cells were then examined through optical microscopy and immunofluorescence techniques. More specifically, the transparency of the PDMS allowed staining in immunofluorescence to be effected directly inside the devices, sequentially perfusing the solutions required in relation to the desired stain, and visualizing the constructs through confocal microscopy, consequently without there being the necessity of extraction from the device. The analysis of the stains for connexin 43 and cardiac troponin showed a greater formation of synergic structures between the cells in the presence of stimulus. The total area of positive construct for connexin 43, normalized for the total number of cardiomyocytes (positive for cardiac troponin) proved in fact to be significantly higher (69.56%±9.05%) for the stimulated constructs with respect to the controls (52.98%±4.03%). This result was then confirmed by the onset of a synchronous beat in the stimulated constructs already 3 days after the beginning of the mechanical stimulation.

Analysis of the Constructs: Pacing

The level of maturation of the cell constructs thus obtained was examined by means of electric pacing after 7 days of culture. The cell constructs were positioned under an inverted microscope to monitor their contractile response during the whole duration of the electric pacing. A temperature of 37° C. and an atmosphere of 5% of $CO_2$ were maintained through an integrated environmental incubation chamber. Two stimulation electrodes were inserted in two of the openings for the entry of the culture medium, respectively opposed with respect to the channel containing the cell construct. Said electrodes were connected to an electrostimulator and used for transferring an electrical stimulus having a controlled form and duration, to the cell construct.

The parameters considered for defining the level of maturation of the construct were the excitation threshold and maximum capture rate.

The excitation threshold was defined as the minimum amplitude of the pacing signal necessary for sustaining the synchronous contraction of the cell constructs. Said excitation threshold, measured by gradually increasing the signal amplitude and keeping the frequency fixed at 1 Hz, proved to be lower for the mechanically stimulated constructs (468 mV/cm) with respect to the control constructs (675 mV/cm).

The maximum capture rate was defined as the highest electrical stimulation frequency at which the constructs are capable of following the electrical stimulus signal with a synchronous contraction. This parameter, measured by gradually increasing the frequency and keeping the signal amplitude fixed, proved to be greater for the stimulated constructs (7 Hz) with respect to the control constructs (4 Hz), showing a higher synergy level.

Example 4

Use of the Device for Drug Screening

The mature cardiac construct generated inside the device, as described in Examples 2 and 3, can be used as in vitro model for drug screening. Once the maturation of the constructs had been verified by electric pacing, as described in Example 3, the same experimental set-up was used for verifying the effect of a drug on the electric response of cardiac constructs. More specifically, the effect of the drug lidocaine, an antiarrhythmic drug, was verified. The drug was diluted in two different concentrations (specifically 1 and 2 µg/ml) in a culture medium and these dilutions were injected in sequence into the device from one of the openings used as entry for the culture medium, and their effect was evaluated by direct observation. A control was obtained by maintaining a cardiac construct in the culture medium without the addition of the drug. The spontaneous contraction frequency is quantified and used as parameter for determining the response of the cardiac construct to the drug, and compared with that obtained for the control cardiac construct. The construct stimulated with increasing concentrations of drug shows a decrease in the contraction frequency with respect to the control. The quantity of drug suspension used for each replicate is equal to 50 µl. The response of the constructs is evaluated 60 seconds after the injection of the drug, keeping the construct at a constant temperature of 37° C.

BIBLIOGRAPHY

Agarwal, A., Goss, J. A., Cho, A, McCain, M. L., Parker, K. K. (2013) Microfluidic heart on a chip for higher throughput pharmacological studies. Lab Chip, 13, 3599-3808.

Huang, P. C., Lu, J., Seon, H.; Lee, A. P., Flanagan, L. A., Kim, H., Putnam, A. J., Jeon, N. L. (2009) Engineering microscale cellular niches for three-dimensional multicellular co-cultures. Lab on a chip, 9, 1740-1748.

Mathur, A., Loskill, P., Shao, K., Huebsch, N., Hong, S G., Marcus, S. G., Marks, N., Mandegar, M., Conklin, B. R., Lee, L. P., Healy, K. E. (2015) Human iPSC-based cardiac microphysiological system for drug screening applications. Scientific Reports, 5:8883, 1-7.

The invention claimed is:

1. A microfluidic device for controlled generation and/or culture and/or maturation of three-dimensional cells and/or tissue constructs, the microfluidic device comprising:
a confinement means configured to define at least one first compartment configured to contain a cellular matrix and at least one second compartment configured to contain a culture medium; and
at least one counter element;
wherein the culture medium is liquid,
wherein the confinement means is hydrophobic,
wherein the confinement means and the at least one counter element are reciprocally mobile between a resting position of the cellular matrix and a compression position of the cellular matrix, and
wherein the confinement means is pervious to the culture medium.

2. The device of claim 1, wherein in the compression position, the at least one counter element is in abutment with the confinement means.

3. The device of claim 1, wherein the confinement means comprises chemically inert material.

4. The device of claim 1, wherein the confinement means comprises a plurality of micropillars.

5. The device of claim 4, wherein the micropillars are positioned in two parallel rows so as to define a microfluidic channel.

6. The device of claim 1, wherein the at least one counter element comprises a mobile wall.

7. The device of claim 1, further comprising:
an actuation chamber configured to cause movement of the at least one counter element toward the cellular matrix to compress the cellular matrix.

8. The device of claim 1, wherein the confinement means is made with one or more of silicon rubber, fluorinated rubber, polystyrene (PS), polymethyl methacrylate (PMMA), polycarbonate (PC), glass, silicon, or polyethyleneglycol (PEG).

9. A microfluidic device for controlled generation and/or culture and/or maturation of three-dimensional cells and/or tissue constructs, the microfluidic device comprising:
a confinement means configured to define at least one first compartment configured to contain a cellular matrix and at least one second compartment configured to contain a culture medium; and
at least one counter element;
wherein the culture medium is liquid,
wherein the confinement means is hydrophobic,
wherein the confinement means and the at least one counter element are reciprocally mobile between a resting position of the cellular matrix and a compression position of the cellular matrix, and
wherein the confinement means is pervious to the culture medium so that, in the compression position, the culture medium contacts the cellular matrix.

10. The device of claim 9, wherein in the compression position, the at least one counter element s in abutment with the confinement means.

11. The device of claim 9, wherein the confinement means comprises chemically inert material.

12. The device of claim 9, wherein the confinement means comprises a plurality of micropillars.

13. The device of claim 9, wherein the at least one counterelement comprises a. mobile wall.

14. The device of claim 9, further comprising:
an actuation chamber configured to cause movement of the at least one counter element toward the cellular matrix to compress the cellular matrix.

15. A microfluidic device for controlled generation and/or culture and/or maturation of three-dimensional cells and/or tissue constructs, the microfluidic device comprising:
a confinement means configured to define at least one first compartment configured to contain a cellular matrix and at least one second compartment configured to contain a culture medium; and
at least one counter element;
wherein the culture medium is liquid,
wherein the confinement means is hydrophobic,
wherein the confinement means and the at least one counter element are reciprocally mobile between a resting position of the cellular matrix and a compression position of the cellular matrix, and
wherein the confinement means is pervious to the culture medium so that, in the compression position, a portion of the culture medium passes from the at least one second compartment into the at least one first compartment.

16. The device of claim 15, wherein in the compression position, the at least one counter element is in abutment with the confinement means.

17. The device of claim 15, wherein the confinement means comprises chemically inert material.

18. The device of claim 15, wherein the confinement means comprises a plurality of micropillars.

19. The device of claim 15, wherein the at least one counter element comprises a mobile wall.

20. The device of claim 15, further comprising:
an actuation chamber configured to cause movement of the at least one counter element toward the cellular matrix to compress the cellular matrix.

* * * * *